United States Patent
Sittenauer et al.

(10) Patent No.: US 11,738,014 B2
(45) Date of Patent: Aug. 29, 2023

(54) NIRAPARIB PARTICLES AND USES THEREOF

(71) Applicant: CRITITECH, INC., Lawrence, KS (US)

(72) Inventors: Jacob Sittenauer, Lawrence, KS (US); Aranza Barreda Abarca, Lawrence, KS (US); Shelby Clark, Lawrence, KS (US); Joseph Farthing, Lawrence, KS (US); Mark Williams, Lawrence, KS (US); Gere Dizerega, Lawrence, KS (US); Michael Baltezor, Lawrence, KS (US)

(73) Assignee: Crititech, Inc., Lawrence, KS (US)

( * ) Notice: Subject to any disclaimer, the term of this patent is extended or adjusted under 35 U.S.C. 154(b) by 0 days.

(21) Appl. No.: 18/053,491

(22) Filed: Nov. 8, 2022

(65) Prior Publication Data

US 2023/0142591 A1    May 11, 2023

Related U.S. Application Data

(60) Provisional application No. 63/277,780, filed on Nov. 10, 2021.

(51) Int. Cl.
| | | |
|---|---|---|
| *A61K 31/454* | (2006.01) | |
| *A61K 9/16* | (2006.01) | |
| *A61K 9/00* | (2006.01) | |

(52) U.S. Cl.
CPC ............ *A61K 31/454* (2013.01); *A61K 9/008* (2013.01); *A61K 9/1688* (2013.01)

(58) Field of Classification Search
CPC ...... A61K 9/008; A61K 9/1688; A61K 9/007; A61K 9/0073; A61K 9/0075; A61K 9/0078; A61K 9/0082
See application file for complete search history.

(56) References Cited

U.S. PATENT DOCUMENTS

| | | |
|---|---|---|
| 2019/0290629 A1 | 9/2019 | Gan et al. |
| 2021/0030735 A1* | 2/2021 | McGurk .............. A61K 9/0056 |
| 2021/0038585 A1 | 2/2021 | McGurk et al. |

FOREIGN PATENT DOCUMENTS

| | | |
|---|---|---|
| WO | 2016/197091 A1 | 12/2016 |
| WO | 2019/067851 A1 | 4/2019 |
| WO | 2019/067866 A1 | 4/2019 |
| WO | 2022/020449 A1 | 1/2022 |
| WO | 2022/020455 A1 | 1/2022 |
| WO | 2022/055958 A1 | 3/2022 |

OTHER PUBLICATIONS

Baltezor et al. "Aggregated High Surface Area Particle Technology for Pulmonary Drug Delivery," Respiratory Drug Delivery 2020, vol. 2, 1020; 329-334. (Year: 2020).*

Sheth et al. "Nanoparticles in the pharmaceutical industry and the use of supercritical fluid technologies for nanoparticle production", Curr Drug Deliv. 9(3): 269-284 (May 2012).

* cited by examiner

*Primary Examiner* — James D. Anderson
*Assistant Examiner* — William Y Lee
(74) *Attorney, Agent, or Firm* — McDonnell Boehnen Hulbert & Berghoff

(57) ABSTRACT

Compositions of particles having at least 95% by weight of niraparib and a specific surface area (SSA) of at least 5 m²/g, methods for their use, and methods for their production are provided.

17 Claims, 5 Drawing Sheets

NIRAPARIB PARTICLES AND USES THEREOF

CROSS REFERENCE

This application claims priority to U.S. Provisional Patent Application Ser. No. 63/277,780 filed Nov. 10, 2021, incorporate by reference herein in its entirety.

BACKGROUND

Dissolution rate is a key parameter in determining the rate and extent of drug absorption and bioavailability. Poor aqueous solubility and poor in vivo dissolution are limiting factors for in vivo bioavailability of many drugs. Thus, in vitro dissolution rates are recognized as an important element in drug development, and methods and compositions for increasing the dissolution rates of poorly soluble drugs are needed.

SUMMARY

In one aspect, the disclosure provides compositions, comprising particles comprising at least 95% by weight of niraparib, or a pharmaceutically acceptable salt thereof, wherein the particles have a specific surface area (SSA) of at least 5 $m^2/g$. In another embodiment, the particles have a SSA of between 5 $m^2/g$ and about 50 $m^2/g$. In a further embodiment, the particles have a mean particle size by volume distribution (Dv50) of from about 1.0 micron to about 10.0 microns in diameter. In one embodiment, the particles have a mean bulk density (not tapped) between about 0.020 $g/cm^3$ and about 0.500 $g/cm^3$. In another embodiment, the particles have a mean tapped density of between about 0.050 $g/cm^3$ and about 0.600 $g/cm^3$.

In one embodiment, the particles are uncoated and exclude polymer, protein, polyethoxylated castor oil and polyethylene glycol glycerides composed of mono-, di- and triglycerides and mono- and diesters of polyethylene glycol. In another embodiment, the composition comprises a suspension further comprising a pharmaceutically acceptable liquid carrier. In one embodiment, the suspension is aerosolized, and the mass median aerodynamic diameter (MMAD) of aerosol droplets of the suspension may be any suitable diameter for use, such as between about 0.5 µm to about 6 µm diameter. In another embodiment, the composition is a dry powder composition, wherein the dry powder composition is aerosolized, and the MMAD of the aerosolized dry powder composition may be any suitable diameter for use, such as between about 0.5 µm to about 6 µm in diameter. In one embodiment, the pharmaceutically acceptable salt of niraparib comprises niraparib tosylate monohydrate.

In another aspect, the disclosure provides methods for treating a tumor, comprising administering to a subject with a tumor an amount effective to treat the tumor of the composition of any embodiment or combination of embodiments of the disclosure. In another aspect, the disclosure provides methods for making niraparib particles, comprising:

(a) introducing (i) a solution comprising at least one solvent including but not limited to ethanol, methanol, hexafluoroisopropanol (HFIP), or combinations thereof, and at least one solute comprising niraparib or a pharmaceutically acceptable salt thereof into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 µm and 125 µm;

(c) contacting the atomized droplets with the compressed fluid, to cause depletion of the solvent from the atomized droplets, to produce niraparib particles comprising at least 95% niraparib or a pharmaceutically acceptable salt thereof, wherein the niraparib particles have a specific surface area (SSA) of at least 5 $m^2/g$, and optionally have mean particle size by volume distribution (Dv50) of from about 1.0 micron to about 10.0 microns in diameter, wherein steps (a), (b), and (c) are carried out under supercritical temperature and pressure for the compressed fluid.

DETAILED DESCRIPTION

Figure 1:
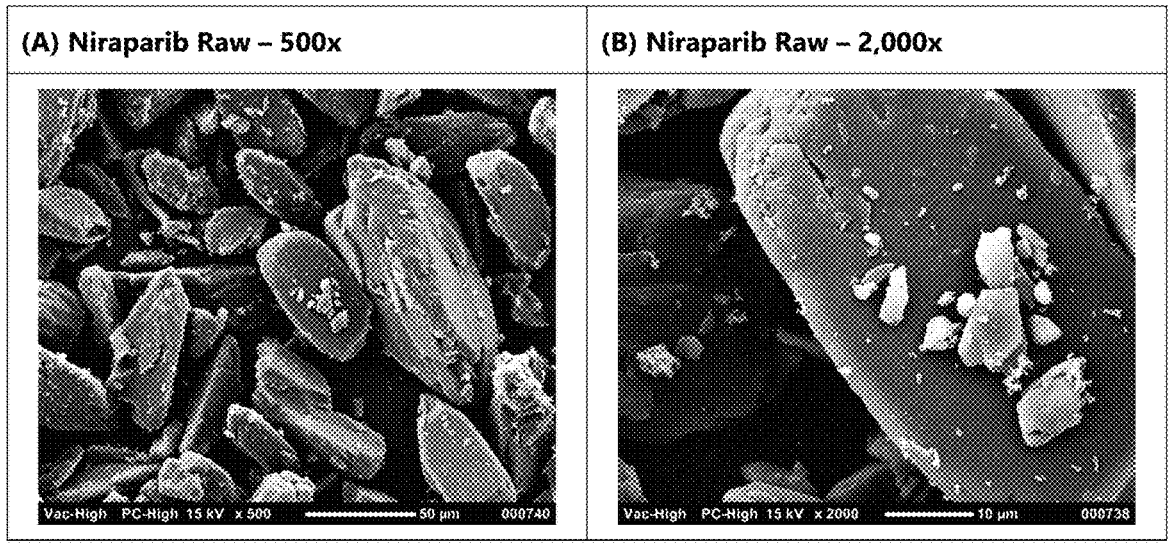
FIG. 1. Scanning Electron Microscopy Micrographs of (A) Raw material niraparib 500X, (B) Raw material niraparib 2000X.
Figure 2:
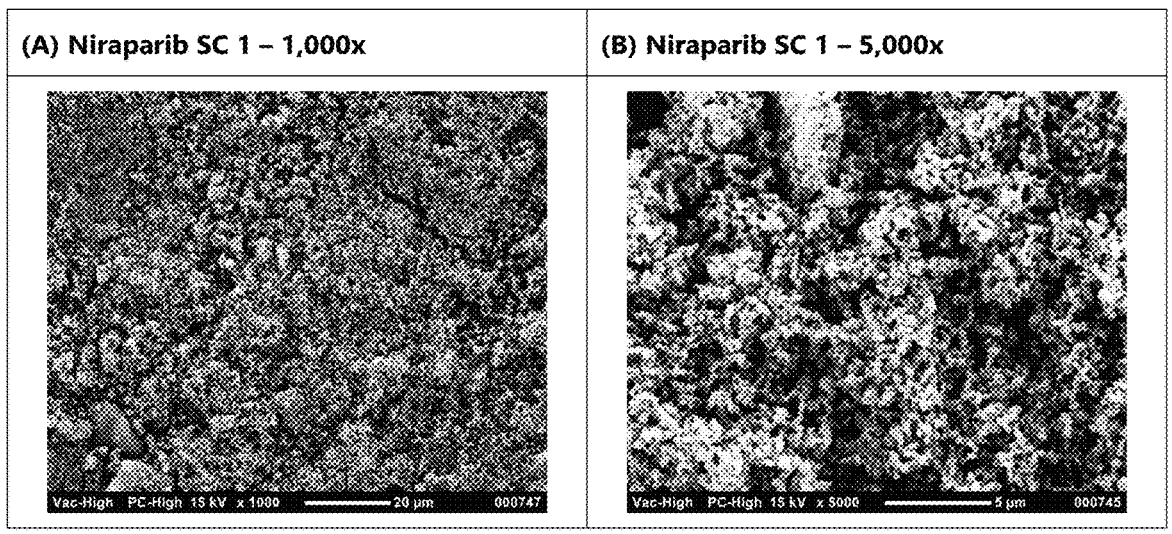
FIG. 2. Scanning Electron Microscopy Micrographs of (A) niraparib SC1 1000X, (B) niraparib SC1 5000X.
Figure 3:
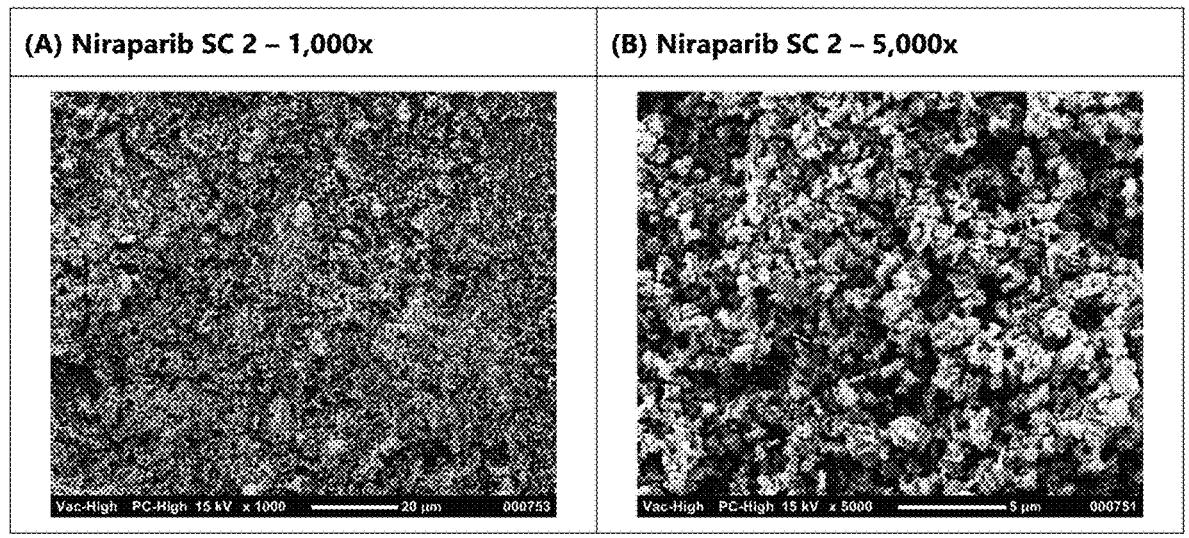
FIG. 3. Scanning Electron Microscopy Micrographs of (A) niraparib SC2 1000X, (B) niraparib SC2 5000X.
Figure 4:
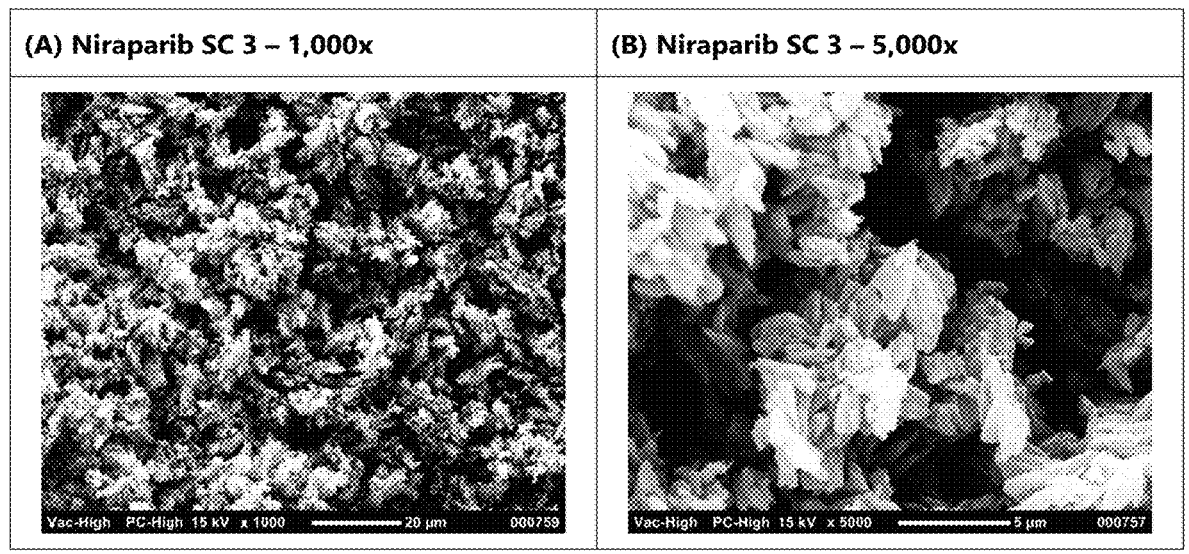
FIG. 4. Scanning Electron Microscopy Micrographs of (A) niraparib SC3 1000X, (B) niraparib SC3 5000X.
Figure 5:
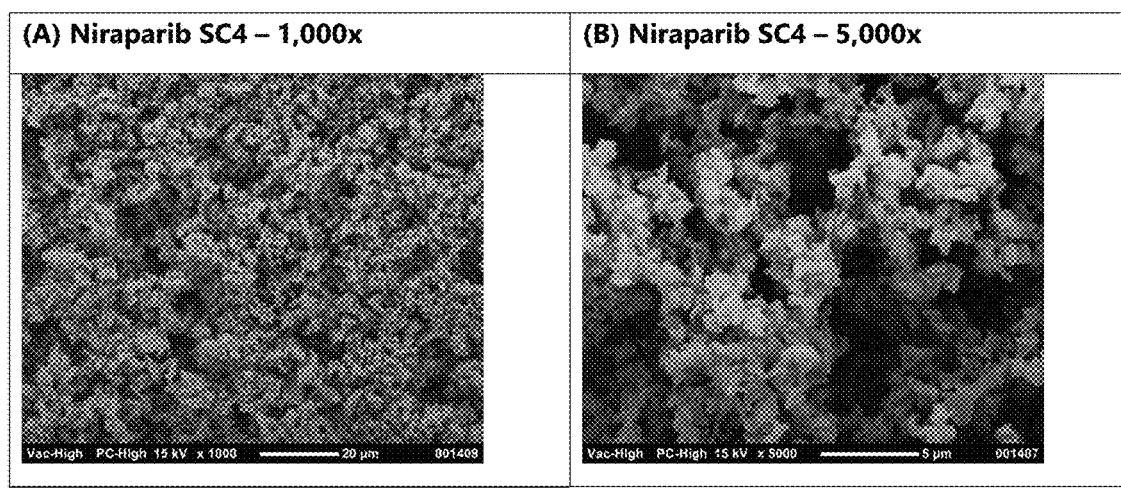
FIG. 5. Scanning Electron Microscopy Micrographs of (A) niraparib SC4 1000X, (B) niraparib SC4 5000X.

All references cited are herein incorporated by reference in their entirety. As used herein, the singular forms "a", "an" and "the" include plural referents unless the context clearly dictates otherwise. All embodiments of any aspect of the disclosure can be used in combination, unless the context clearly dictates otherwise.

As used herein, "about" means +/−5% of the recited value.

In one aspect, the disclosure provides compositions, comprising particles comprising at least 95% by weight of niraparib, or a pharmaceutically acceptable salt thereof, wherein the particles have a specific surface area (SSA) of at least 5 $m^2/g$. Such particles are referred to herein as "niraparib particles."

As used herein, "niraparib" includes any ionization state of niraparib, including base, acid, and neutral states.

Structure of niraparib

Niraparib chemical name: (S)-2-(4-(piperidin-3-yl)phenyl)-2H-indazole-7-carboxamide The "niraparib particles" refers to particles of niraparib, or a pharmaceutically acceptable salt thereof, which do not include an added excipient. Niraparib particles are different than "particles containing niraparib", which are particles that contain niraparib and at least one added excipient. Niraparib particles of the disclosure exclude a polymeric, wax or protein excipient and are not embedded, contained, enclosed or encapsulated within a solid excipient. Niraparib particles of the disclosure may, however, contain impurities and byproducts typically found during preparation of niraparib. Even so, niraparib particles comprise at least 95%, at least 96%, at least 97%, at least 98%, at least 99% or 100% niraparib, or a pharmaceutically acceptable salt thereof, meaning the niraparib particles consist of or consist essentially of substantially pure niraparib or pharmaceutically acceptable salt of niraparib.

As used herein, the "specific surface area" is the total surface area of the niraparib particle per unit of niraparib mass as measured by the Brunauer-Emmett-Teller ("BET") isotherm (i.e.: the BET SSA). As will be understood by those of skill in the art, the SSA is determined on a per gram basis and takes into account both agglomerated and non-agglomerated niraparib particles in the composition. The BET specific surface area test procedure is a compendial method included in both the United States Pharmacopeia and the European Pharmacopeia. The niraparib particles have a specific surface area (SSA) of at least 5 $m^2/g$. In various further embodiments, the niraparib particles have a SSA of at least 6 $m^2/g$, 7 $m^2/g$, 8 $m^2/g$, 9 $m^2/g$ 10 $m^2/g$, 11 $m^2/g$, 12 $m^2/g$, 13 $m^2/g$, 14 $m^2/g$, 15 $m^2/g$, 16 $m^2/g$, 17 $m^2/g$, 18 $m^2/g$, 19 $m^2/g$, 20 $m^2/g$, 21 $m^2/g$, 22 $m^2/g$, 23 $m^2/g$, or 24 $m^2/g$.

In further embodiments, the niraparib particles have a SSA of between 5 $m^2/g$ and about 50 $m^2/g$, between about 6 $m^2/g$ and about 50 $m^2/g$, between about 7 $m^2/g$ and about 50 $m^2/g$, between about 8 $m^2/g$ and about 50 $m^2/g$, between about 9 $m^2/g$ and about 50 $m^2/g$, between about 10 $m^2/g$ and about 50 $m^2/g$, between about 11 $m^2/g$ and about 50 $m^2/g$, between about 12 $m^2/g$ and about 50 $m^2/g$, between about 13 $m^2/g$ and about 50 $m^2/g$, between about 14 $m^2/g$ and about 50 $m^2/g$, between about 15 $m^2/g$ and about 50 $m^2/g$, between about 16 $m^2/g$ and about 50 $m^2/g$, between about 17 $m^2/g$ and about 50 $m^2/g$, between about 18 $m^2/g$ and about 50 $m^2/g$, between about 19 $m^2/g$ and about 50 $m^2/g$, between about 20 $m^2/g$ and about 50 $m^2/g$, between about 21 $m^2/g$ and about 50 $m^2/g$, between about 22 $m^2/g$ and about 50 $m^2/g$, between about 23 $m^2/g$ and about 50 $m^2/g$, between about 24 $m^2/g$ and about 50 $m^2/g$, between 5 $m^2/g$ and about 45 $m^2/g$, between about 6 $m^2/g$ and about 45 $m^2/g$, between about 7 $m^2/g$ and about 45 $m^2/g$, between about 8 $m^2/g$ and about 45 $m^2/g$, between about 9 $m^2/g$ and about 45 $m^2/g$, between about 10 $m^2/g$ and about 45 $m^2/g$, between about 11 $m^2/g$ and about 45 $m^2/g$, between about 12 $m^2/g$ and about 45 $m^2/g$, between about 13 $m^2/g$ and about 45 $m^2/g$, between about 14 $m^2/g$ and about 45 $m^2/g$, between about 15 $m^2/g$ and about 45 $m^2/g$, between about 16 $m^2/g$ and about 45 $m^2/g$, between about 17 $m^2/g$ and about 45 $m^2/g$, between about 18 $m^2/g$ and about 45 $m^2/g$, between about 19 $m^2/g$ and about 45 $m^2/g$, between about 20 $m^2/g$ and about 45 $m^2/g$, between about 21 $m^2/g$ and about 45 $m^2/g$, between about 22 $m^2/g$ and about 45 $m^2/g$, between about 23 $m^2/g$ and about 45 $m^2/g$, between about 24 $m^2/g$ and about 45 $m^2/g$, between 5 $m^2/g$ and about 40 $m^2/g$, between about 6 $m^2/g$ and about 40 $m^2/g$, between about 7 $m^2/g$ and about 40 $m^2/g$, between about 8 $m^2/g$ and about 40 $m^2/g$, between about 9 $m^2/g$ and about 40 $m^2/g$, between about 10 $m^2/g$ and about 40 $m^2/g$, between about 11 $m^2/g$ and about 40 $m^2/g$, between about 12 $m^2/g$ and about 40 $m^2/g$, between about 13 $m^2/g$ and about 40 $m^2/g$, between about 14 $m^2/g$ and about 40 $m^2/g$, between about 15 $m^2/g$ and about 40 $m^2/g$, between about 16 $m^2/g$ and about 40 $m^2/g$, between about 17 $m^2/g$ and about 40 $m^2/g$, between about 18 $m^2/g$ and about 40 $m^2/g$, between about 19 $m^2/g$ and about 40 $m^2/g$, between about 20 $m^2/g$ and about 40 $m^2/g$, between about 21 $m^2/g$ and about 40 $m^2/g$, between about 22 $m^2/g$ and about 40 $m^2/g$, between about 23 $m^2/g$ and about 40 $m^2/g$, between about 24 $m^2/g$ and about 40 $m^2/g$, between 5 $m^2/g$ and about 35 $m^2/g$, between about 6 $m^2/g$ and about 35 $m^2/g$, between about 7 $m^2/g$ and about 35 $m^2/g$, between about 8 $m^2/g$ and about 35 $m^2/g$, between about 9 $m^2/g$ and about 35 $m^2/g$, between about 10 $m^2/g$ and about 35 $m^2/g$, between about 11 $m^2/g$ and about 35 $m^2/g$, between about 12 $m^2/g$ and about 35 $m^2/g$, between about 13 $m^2/g$ and about 35 $m^2/g$, between about 14 $m^2/g$ and about 35 $m^2/g$, between about 15 $m^2/g$ and about 35 $m^2/g$, between about 16 $m^2/g$ and about 35 $m^2/g$, between about 17 $m^2/g$ and about 35 $m^2/g$, between about 18 $m^2/g$ and about 35 $m^2/g$, between about 19 $m^2/g$ and about 35 $m^2/g$, between about 20 $m^2/g$ and about 35 $m^2/g$, between about 21 $m^2/g$ and about 35 $m^2/g$, between about 22 $m^2/g$ and about 35 $m^2/g$, between about 23 $m^2/g$ and about 35 $m^2/g$, between about 24 $m^2/g$ and about 35 $m^2/g$, between 5 $m^2/g$ and about 30 $m^2/g$, between about 6 $m^2/g$ and about 30 $m^2/g$, between about 7 $m^2/g$ and about 30 $m^2/g$, between about 8 $m^2/g$ and about 30 $m^2/g$, between about 9 $m^2/g$ and about 30 $m^2/g$, between about 10 $m^2/g$ and about 30 $m^2/g$, between about 11 $m^2/g$ and about 30 $m^2/g$, between about 12 $m^2/g$ and about 30 $m^2/g$, between about 13 $m^2/g$ and about 30 $m^2/g$, between about 14 $m^2/g$ and about 30 $m^2/g$, between about 15 $m^2/g$ and about 30 $m^2/g$, between about 16 $m^2/g$ and about 30 $m^2/g$, between about 17 $m^2/g$ and about 30 $m^2/g$, between about 18 $m^2/g$ and about 30 $m^2/g$, between about 19 $m^2/g$ and about 30 $m^2/g$, between about 20 $m^2/g$ and about 30 $m^2/g$, between about 21 $m^2/g$ and about 30 $m^2/g$, between about 22 $m^2/g$ and about 30 $m^2/g$, between about 23 $m^2/g$ and about 30 $m^2/g$, or between about 24 $m^2/g$ and about 30 $m^2/g$.

In one embodiment, the niraparib particles have a mean particle size by volume distribution (Dv50) of from about 1.0 micron to about 10.0 microns in diameter. In some embodiments, the niraparib particles have a mean particle size by volume distribution of from about 1 micron to about 6 microns in diameter, or about 2 microns to about 6 microns in diameter. The niraparib particles are in a size range where they are unlikely to be carried out of the tumor by systemic circulation and yet benefit from the high specific surface area to provide enhanced solubilization and release of the drug.

In one embodiment, the niraparib particles have a mean bulk density (not tapped) between about 0.020 $g/cm^3$ and about 0.500 $g/cm^3$. In various further embodiments, the niraparib particles have a mean bulk density (not tapped) between about 0.020 $g/cm^3$ and about 0.475 $g/cm^3$, between about 0.020 $g/cm^3$ and about 0.450 $g/cm^3$, between about 0.020 $g/cm^3$ and about 0.425 $g/cm^3$, between about 0.020 $g/cm^3$ and about 0.400 $g/cm^3$, between about 0.020 $g/cm^3$ and about 0.375 $g/cm^3$, between about 0.020 $g/cm^3$ and about 0.350 $g/cm^3$, between about 0.020 $g/cm^3$ and about 0.325 $g/cm^3$, between about 0.020 $g/cm^3$ and about 0.300 $g/cm^3$, between ab out 0.020 $g/cm^3$ and about 0.275 $g/cm^3$, between about 0.020 $g/cm^3$ and about 0.250 $g/cm^3$, between about 0.020 $g/cm^3$ and about 0.225 $g/cm^3$, between about 0.020 $g/cm^3$ and about 0.200 $g/cm^3$, between about 0.020 $g/cm^3$ and about 0.175 $g/cm^3$, between about 0.020 $g/cm^3$ and about 0.150 g/cm³, between about 0.020 g/cm³ and about 0.125 g/cm³, between about 0.020 g/cm³ and about 0.100 g/cm³, between about 0.040 g/cm³ and about 0.475 g/cm³, between about 0.040 g/cm³ and about 0.450 g/cm³, between about 0.040 g/cm³ and about 0.425 g/cm³, between about 0.040 g/cm³ and about 0.400 g/cm³, between about 0.040 g/cm³ and about 0.375 g/cm³, between about 0.040 g/cm³ and about 0.350 g/cm³, between about 0.040 g/cm³ and about 0.325 g/cm³, between about 0.040 g/cm³ and about 0.300 g/cm³, between about 0.040 g/cm³ and about 0.275 g/cm³, between about 0.040 g/cm³ and about 0.250 g/cm³, between about 0.040 g/cm³ and about 0.225 g/cm³, between about 0.040 g/cm³ and about 0.200 g/cm³, between about 0.040 g/cm³ and about 0.175 g/cm³, between about 0.040 g/cm³ and about 0.150 g/cm³, between about 0.040 g/cm³ and about 0.125 g/cm³, between about 0.040 g/cm³ and about 0.100 g/cm³, between about 0.060 g/cm³ and about 0.475 g/cm³, between about 0.060 g/cm³ and about 0.450 g/cm³, between about 0.060 g/cm³ and about 0.425 g/cm³, between about 0.060 g/cm³ and about 0.400 g/cm³, between about 0.060 g/cm³ and about 0.375 g/cm³, between about 0.060 g/cm³ and about 0.350 g/cm³, between about 0.060 g/cm³ and about 0.325 g/cm³, between about 0.060 g/cm³ and about 0.300 g/cm³, between about 0.060 g/cm³ and about 0.275 g/cm³, between about 0.060 g/cm³ and about 0.250 g/cm³, between about 0.060 g/cm³ and about 0.225 g/cm³, between about 0.060 g/cm³ and about 0.200 g/cm³, between about 0.060 g/cm³ and about 0.175 g/cm³, between about 0.060 g/cm³ and about 0.150 g/cm³, between about 0.060 g/cm³ and about 0.125 g/cm³, or between about 0.060 g/cm³ and about 0.100 g/cm³.

In another embodiment, the niraparib particles have a mean tapped density of between about 0.050 g/cm³ and about 0.600 g/cm³. In various further embodiments, the niraparib particles have a mean tapped density between about 0.050 g/cm³ and about 0.575 g/cm³, between about 0.050 g/cm³ and about 0.550 g/cm³, between about 0.050 g/cm³ and about 0.525 g/cm³, between about 0.050 g/cm³ and about 0.500 g/cm³, between about 0.050 g/cm³ and about 0.475 g/cm³, between about 0.050 g/cm³ and about 0.450 g/cm³, between about 0.050 g/cm³ and about 0.425 g/cm³, between about 0.050 g/cm³ and about 0.400 g/cm³, between about 0.050 g/cm³ and about 0.375 g/cm³, between about 0.050 g/cm³ and about 0.350 g/cm³, between about 0.050 g/cm³ and about 0.325 g/cm³, between about 0.050 g/cm³ and about 0.300 g/cm³, between about 0.050 g/cm³ and about 0.275 g/cm³, between about 0.050 g/cm³ and about 0.250 g/cm³, between about 0.050 g/cm³ and about 0.225 g/cm³, between about 0.050 g/cm³ and about 0.200 g/cm³, between about 0.050 g/cm³ and about 0.175 g/cm³, between about 0.050 g/cm³ and about 0.150 g/cm³, between about 0.050 g/cm³ and about 0.125 g/cm³, between about 0.075 g/cm³ and about 0.575 g/cm³, between about 0.075 g/cm³ and about 0.550 g/cm³, between about 0.075 g/cm³ and about 0.525 g/cm³, between about 0.075 g/cm³ and about 0.500 g/cm³, between about 0.075 g/cm³ and about 0.475 g/cm³, between about 0.075 g/cm³ and about 0.450 g/cm³, between about 0.075 g/cm³ and about 0.425 g/cm³, between about 0.075 g/cm³ and about 0.400 g/cm³, between about 0.075 g/cm³ and about 0.375 g/cm³, between about 0.075 g/cm³ and about 0.350 g/cm³, between about 0.075 g/cm³ and about 0.325 g/cm³, between about 0.075 g/cm³ and about 0.300 g/cm³, between about 0.075 g/cm³ and about 0.275 g/cm³, between about 0.075 g/cm³ and about 0.250 g/cm³, between about 0.075 g/cm³ and about 0.225 g/cm³, between about 0.075 g/cm³ and about 0.200 g/cm³, between about 0.075 g/cm³ and about 0.175 g/cm³, between about 0.075 g/cm³ and about 0.150 g/cm³, between about 0.075 g/cm³ and about 0.125 g/cm³, between about 0.100 g/cm³ and about 0.575 g/cm³, between about 0.100 g/cm³ and about 0.550 g/cm³, between about 0.100 g/cm³ and about 0.525 g/cm³, between about 0.100 g/cm³ and about 0.500 g/cm³, between about 0.100 g/cm³ and about 0.475 g/cm³, between about 0.100 g/cm³ and about 0.450 g/cm³, between about 0.100 g/cm³ and about 0.425 g/cm³, between about 0.100 g/cm³ and about 0.400 g/cm³, between about 0.100 g/cm³ and about 0.375 g/cm³, between about 0.100 g/cm³ and about 0.350 g/cm³, between about 0.100 g/cm³ and about 0.325 g/cm³, between about 0.100 g/cm³ and about 0.300 g/cm³, between about 0.100 g/cm³ and about 0.275 g/cm³, between about 0.100 g/cm³ and about 0.250 g/cm³, between about 0.100 g/cm³ and about 0.225 g/cm³, between about 0.100 g/cm³ and about 0.200 g/cm³, between about 0.100 g/cm³ and about 0.175 g/cm³, between about 0.100 g/cm³ and about 0.150 g/cm³, or between about 0.100 g/cm³ and about 0.125 g/cm³.

As used herein, the bulk density (not tapped) of a particle is the ratio of the mass to the volume (including the interparticulate void volume) of an untapped powder sample.

As used herein, the tapped density of a particle is obtained by mechanically tapping a graduated cylinder containing the sample until little further volume change is observed.

The increased specific surface area and decreased bulk density of the niraparib particles result in significant increases in dissolution rate compared to, for example, raw or milled niraparib products. Dissolution takes place only at a solid/liquid interface. Therefore, increased specific surface area will increase the dissolution rate due to a larger number of molecules on the surface of the particle having contact with the dissolution media. The bulk density takes into account the macrostructure and inter-particle space of a powder. Parameters that contribute to the bulk density include particle size distribution, particle shape, and the affinity of the particles for each other (i.e., agglomeration). Lower powder bulk densities yield faster dissolution rates. This is due to the ability of the dissolution media to more readily penetrate the interstitial or inter-particle spaces and have greater contact with the surface of the particles. This provides a significant improvement for use of the niraparib particles disclosed herein in, for example, tumor treatment.

In any of these various embodiments, the niraparib particles may include, for example, at least $5 \times 10^{-15}$ gram niraparib or a pharmaceutically acceptable salt thereof per niraparib particle, or between about $1 \times 10^{-8}$ and about $5 \times 10^{-15}$ gram niraparib, or a pharmaceutically acceptable salt thereof per niraparib particle.

In one embodiment, the particles are uncoated and exclude polymer, protein, polyethoxylated castor oil and polyethylene glycol glycerides composed of mono-, di- and triglycerides and mono- and diesters of polyethylene glycol.

In a further embodiment, the composition comprises a liquid suspension further comprising a pharmaceutically acceptable liquid carrier. The suspension of the disclosure comprises niraparib particles and a liquid carrier. The liquid carrier can be aqueous or can be non-aqueous. Even though the niraparib particles do not include an added excipient, the liquid carrier of the suspension can comprise water or a non-aqueous liquid and optionally one or more excipients selected from the group consisting of buffer, tonicity adjusting agent, preservative, demulcent, viscosity modifier, osmotic agent, surfactant, antioxidant, alkalinizing agent, acidifying agent, antifoaming agent, and colorant. For example, the suspension can comprise niraparib particles, water, buffer and salt. It optionally further comprises a surfactant. In some embodiments, the suspension consists essentially of or consists of water, niraparib particles suspended in the water and buffer. The suspension can further contain an osmotic salt. In another example, the suspension can comprise niraparib particles and a non-aqueous liquid such as a liquefied gas propellant. Examples of a liquefied gas propellant include but are not limited to hydrofluoroalkanes (HFAs). Examples of other non-aqueous liquids include but are not limited to mineral oils, vegetable oils, glycerin, polyethylene glycol, poloxamers that are liquid at room temperature (e.g., poloxamer 124), and polyethylene glycols that are liquid at room temperature, (e.g., PEG 400 and PEG 600).

In one embodiment, the suspension further comprises one or more components selected from the group consisting of polysorbate, methylcellulose, polyvinylpyrrolidone, mannitol, and hydroxypropyl methylcellulose.

The suspension can comprise one or more surfactants. Suitable surfactants include by way of example and without limitation polysorbates, lauryl sulfates, acetylated monoglycerides, diacetylated monoglycerides, and poloxamers.

The suspension can comprise one or more tonicity adjusting agents. Suitable tonicity adjusting agents include by way of example and without limitation, one or more inorganic salts, electrolytes, sodium chloride, potassium chloride, sodium phosphate, potassium phosphate, sodium, potassium sulfates, sodium and potassium bicarbonates and alkaline earth metal salts, such as alkaline earth metal inorganic salts, e.g., calcium salts, and magnesium salts, mannitol, dextrose, glycerin, propylene glycol, and mixtures thereof.

In one embodiment especially suitable for intraperitoneal (IP) administration, the suspension may be formulated to be hyperosmolar (hypertonic), hyposmolar (hypotonic) or isosmolar (isotonic) with respect to the fluid(s) of the IP cavity. In some embodiments, the suspension may be isotonic with respect to fluid in the IP cavity. In such an embodiment, the osmolality of the suspension can range from about 200 to about 380, about 240 to about 340, about 280 to about 300 or about 290 mOsm/kg.

The suspension can comprise one or more buffering agents. Suitable buffering agents include by way of example and without limitation, dibasic sodium phosphate, monobasic sodium phosphate, citric acid, sodium citrate hydrochloric acid, sodium hydroxide, tris(hydroxymethyl)aminomethane, bis(2-hydroxyethyl)iminotris-(hydroxymethyl)methane, and sodium hydrogen carbonate and others known to those of ordinary skill in the art. Buffers are commonly used to adjust the pH to a desirable range for intraperitoneal use. Usually a pH of around 5 to 9, 5 to 8, 6 to 7.4, 6.5 to 7.5, or 6.9 to 7.4 is desired.

The suspension can comprise one or more demulcents. A demulcent is an agent that forms a soothing film over a mucous membrane, such as the membranes lining the peritoneum and organs therein. A demulcent may relieve minor pain and inflammation and is sometimes referred to as a mucoprotective agent. Suitable demulcents include cellulose derivatives ranging from about 0.2 to about 2.5% such as carboxymethylcellulose sodium, hydroxyethyl cellulose, hydroxypropyl methylcellulose, and methylcellulose; gelatin at about 0.01%; polyols in about 0.05 to about 1%, also including about 0.05 to about 1%, such as glycerin, polyethylene glycol 300, polyethylene glycol 400, polysorbate 80, and propylene glycol; polyvinyl alcohol from about 0.1 to about 4%; povidone from about 0.1 to about 2%; and dextran 70 from about 0.1% when used with another polymeric demulcent described herein.

The suspension can comprise one or more alkalinizing agents to adjust the pH. As used herein, the term "alkalizing agent" is intended to mean a compound used to provide an alkaline medium. Such compounds include, by way of example and without limitation, ammonia solution, ammonium carbonate, potassium hydroxide, sodium carbonate, sodium bicarbonate, and sodium hydroxide and others known to those of ordinary skill in the art The suspension can comprise one or more acidifying agents to adjust the pH. As used herein, the term "acidifying agent" is intended to mean a compound used to provide an acidic medium. Such compounds include, by way of example and without limitation, acetic acid, amino acid, citric acid, nitric acid, fumaric acid and other alpha hydroxy acids, hydrochloric acid, ascorbic acid, and nitric acid and others known to those of ordinary skill in the art.

The suspension can comprise one or more antifoaming agents. As used herein, the term "antifoaming agent" is intended to mean a compound or compounds that prevents or reduces the amount of foaming that forms on the surface of the fill composition. Suitable antifoaming agents include by way of example and without limitation, dimethicone, SIMETHICONE®, octoxynol and others known to those of ordinary skill in the art.

The suspension can comprise one or more viscosity modifiers that increase or decrease the viscosity of the suspension. Suitable viscosity modifiers include methylcellulose, hydroxypropyl methycellulose, mannitol and polyvinylpyrrolidone.

The suspension can comprise one or more osmotic agents such as those used for peritoneal dialysis. Suitable osmotic agents include icodextrin (a glucose polymer), sodium chloride, potassium chloride, and salts that are also used as buffering agents.

In one embodiment, a liquid suspension of the niraparib particles may be aerosolized for pulmonary administration by inhalation, and the mass median aerodynamic diameter (MMAD) of the aerosol droplets of the liquid suspension may be any suitable diameter for use. In one embodiment, the aerosol droplets have a MMAD of between about 0.5 μm to about 6 μm diameter. In various further embodiments, the aerosol droplets have a MMAD of between about 0.5 μm to about 5.5 μm diameter, about 0.5 μm to about 5 μm diameter, about 0.5 μm to about 4.5 μm diameter, about 0.5 μm to about 4 μm diameter, about 0.5 μm to about 3.5 μm diameter, about 0.5 μm to about 3 μm diameter, about 0.5 μm to about 2.5 μm diameter, about 0.5 μm to about 2 μm diameter, about 1 μm to about 5.5 μm diameter, about 1 μm to about 5 μm diameter, about 1 μm to about 4.5 μm diameter, about 1 μm to about 4 μm diameter, about 1 μm to about 3.5 μm diameter, about 1 μm to about 3 μm diameter, about 1 μm to about 2.5 μm diameter, about 1 μm to about 2 μm diameter, about 1.5 μm to about 5.5 μm diameter, about 1.5 μm to about 5 μm diameter, about 1.5 μm to about 4.5 μm diameter, about 1.5 μm to about 4 μm diameter, about 1.5 μm to about 3.5 μm diameter, about 1.5 μm to about 3 μm diameter, about 1.5 μm to about 2.5 μm diameter, about 1.5 μm to about 2 μm diameter, about 2 μm to about 5.5 μm diameter, about 2 μm to about 5 μm diameter, about 2 μm to about 4.5 μm diameter, about 2 μm to about 4 μm diameter, about 2 μm to about 3.5 μm diameter, about 2 μm to about 3 μm diameter, and about 2 μm to about 2.5 μm diameter. A suitable instrument for measuring the mass median aerodynamic diameter (MMAD) and geometric standard deviation (GSD) of the aerosol droplets is a seven-stage aerosol sampler such as the Mercer-Style Cascade Impactor. Liquid suspensions of niraparib particles delivered by aerosol may be deposited in the airways by gravitational sedimentation, inertial impaction, and/or diffusion. Any suitable device for generating the aerosol may be used, including but not limited to metered dose inhalers (MDI), pressured metered dose inhalers (pMDI), nebulizers, and soft-mist inhalers.

In one embodiment, a dry powder composition of niraparib particles may be aerosolized for pulmonary administration by inhalation, and the mass median aerodynamic diameter (MMAD) of the aerosolized dry powder composition may be any suitable diameter for use. The dry powder composition is formulated as a dry powder. The dry powder composition can contain niraparib particles alone without a carrier or can comprise niraparib particles and a pharmaceutically acceptable dry powder carrier comprising one or more dry powder excipients. In one embodiment, the aerosolized dry powder composition has a MMAD of between about 0.5 μm to about 6 μm diameter. In various further embodiments, the aerosolized dry powder composition has a MMAD of between about 0.5 μm to about 5.5 μm diameter, about 0.5 μm to about 5 μm diameter, about 0.5 μm to about 4.5 μm diameter, about 0.5 μm to about 4 μm diameter, about 0.5 μm to about 3.5 μm diameter, about 0.5 μm to about 3 μm diameter, about 0.5 μm to about 2.5 μm diameter, about 0.5 μm to about 2 μm diameter, about 1 μm to about 5.5 μm diameter, about 1 μm to about 5 μm diameter, about 1 μm to about 4.5 μm diameter, about 1 μm to about 4 μm diameter, about 1 μm to about 3.5 μm diameter, about 1 μm to about 3 μm diameter, about 1 μm to about 2.5 μm diameter, about 1 μm to about 2 μm diameter, about 1.5 μm to about 5.5 μm diameter, about 1.5 μm to about 5 μm diameter, about 1.5 μm to about 4.5 μm diameter, about 1.5 μm to about 4 μm diameter, about 1.5 μm to about 3.5 μm diameter, about 1.5 μm to about 3 μm diameter, about 1.5 μm to about 2.5 μm diameter, about 1.5 μm to about 2 μm diameter, about 2 μm to about 5.5 μm diameter, about 2 μm to about 5 μm diameter, about 2 μm to about 4.5 μm diameter, about 2 μm to about 4 μm diameter, about 2 μm to about 3.5 μm diameter, about 2 μm to about 3 μm diameter, and about 2 μm to about 2.5 μm diameter. A suitable instrument for measuring the mass median aerodynamic diameter (MMAD) and geometric standard deviation (GSD) of the dry powder composition is a seven-stage aerosol sampler such as the Mercer-Style Cascade Impactor or an aerodynamic particle sizer spectrometer such as the APS™ Model 3321 spectrometer available from TSI Incorporated. The dry powder composition delivered by aerosol may be deposited in the airways by gravitational sedimentation, inertial impaction, and/or diffusion. Any suitable device for generating the aerosol of the dry powder composition may be used, including but not limited to dry powder inhalers (DPI). An example of an excipient suitable for a dry powder inhalable composition includes but is not limited to lactose in grades suitable for inhalation. In one embodiment, the composition is a dry powder composition suitable for pulmonary delivery by inhalation via aerosolization.

As used herein, "pharmaceutically acceptable salts" of niraparib are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the niraparib. The term "salts" refers to the relatively non-toxic, inorganic and organic acid addition salts of niraparib. Representative salts include the hydrobromide, hydrochloride, sulfate, bisulfate, nitrate, acetate, oxalate, valerate, oleate, palmitate, stearate, laurate, malate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.) In one embodiment, the pharmaceutically acceptable salt of niraparib comprises niraparib tosylate monohydrate is 2-{4-[(3S)-piperidin-3-yl]phenyl}-2H-indazole 7-carboxamide 4-methylbenzenesulfonate hydrate (1:1:1).

In one embodiment, the composition comprises a dosage form of niraparib in suspension (i.e.: with a pharmaceutically acceptable carrier and any other components), in a dosage deemed suitable by an attending physician for an intended use. Any suitable dosage form may be used; in various non-limiting embodiments, the dosage form is adequate to provide about 0.01 mg/kg to about 50 mg/kg of body weight per day. In various further embodiments, the dosage form is adequate to provide about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg of body weight per day. The suspension can be administered as is or can be diluted with a diluent, e.g. with saline water for injection optionally including a buffering agent and one or more other excipients, prior to administration. For example, the volume ratio of suspension to diluent might be in the range of 1:1-1:100 (v/v) or other suitable ratio.

In another aspect, the disclosure provides methods for treating a tumor, comprising administering to a subject with a tumor an amount effective to treat the tumor of the composition or suspension of any embodiment or combination of embodiments of the disclosure. The increased specific surface area of the niraparib particles of the disclosure results in the significant increase in dissolution rate for the particles compared to currently available niraparib. This provides a significant improvement for use of the particles of the disclosure in, for example, tumor treatment. Furthermore, in some embodiments the methods of the present disclosure can reduce the dosing frequency and side effects of niraparib. By way of non-limiting example, a niraparib dose administered by direct tumoral injection would be substantially less and the dosing frequency would be less compared to oral dosing, and side effects would also be expected to be lower since the systemic concentrations would be greatly reduced.

As used herein, a "tumor" includes benign tumors, premalignant tumors, malignant tumors that have not metastasized, and malignant tumors that have metastasized. The methods of the disclosure can be used to treat tumor that is susceptible to niraparib treatment, including but not limited to carcinomas, breast tumors, pancreatic tumors, prostate tumors, fallopian tube tumors, peritoneal tumors, bladder tumors, lung tumors, ovarian tumors, gastrointestinal tumors, testicular tumors, cervical tumors, head and neck tumors, esophageal tumors, mesothelioma, brain tumors, neuroblastomas, or renal cell tumors. In specific embodiments, the tumor is a fallopian tube tumor, peritoneal tumor, or ovarian tumor; in other embodiments, the tumor is an advanced epithelial ovarian, fallopian tube, or primary peritoneal tumor.

In another embodiment, the method further comprises administering an additional therapeutic to the subject, including but not limited to anthracyclines, antimetabolites, alkylating agents (including but not limited to cisplatin), alkaloids, taxanes (including but not limited to paclitaxel, docetaxel, cabazitaxel, and combinations thereof), and/or topoisomerase inhibitors.

The subject may be any suitable subject with a tumor, including but not limited to humans, primates, dogs, cats, horses, cattle, etc. In one embodiment, the subject is a human subject. In some embodiments, the subject, such as a human subject, has (i) advanced epithelial ovarian, fallopian tube, or primary peritoneal cancer who are in a complete or partial response to first-line platinum-based chemotherapy, (ii) recurrent epithelial ovarian, fallopian tube, or primary peritoneal cancer who are in a complete or partial response to platinum-based chemotherapy, or (iii) advanced ovarian, fallopian tube, or primary peritoneal cancer who have been treated with 3 or more prior chemotherapy regimens and whose cancer is associated with homologous recombination deficiency (HRD) positive status defined by either:
  a deleterious or suspected deleterious BRCA mutation, or
  genomic instability and who have progressed more than 6 months after response to the last platinum-based chemotherapy.

As used herein, "treat" or "treating" means accomplishing one or more of the following: (a) reducing the severity of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

Amounts effective for these uses depend on factors including, but not limited to, the nature of the niraparib (specific activity, etc.), the route of administration, the stage and severity of the disorder, the weight and general state of health of the subject, and the judgment of the prescribing physician. It will be understood that the amount of the composition of suspension of the disclosure actually administered will be determined by a physician, in the light of the above relevant circumstances. In one non-limiting embodiment, an amount effective is an amount that provides between 0.01 mg/kg to about 50 mg/kg of body weight per day.

In a further embodiment, the composition comprises a liquid suspension further comprising a pharmaceutically acceptable liquid carrier. The suspension of the disclosure comprises niraparib particles and a liquid carrier. All embodiments of the suspension and liquid carrier, disclosed herein may be used in therapeutic methods of the disclosure.

In one embodiment, a liquid suspension of the niraparib particles for therapeutic use may be aerosolized for pulmonary administration by inhalation, and the mass median aerodynamic diameter (MMAD) of the aerosol droplets of the liquid suspension may be any suitable diameter for use, and all embodiments disclosed herein may be used in the therapeutic methods of the disclosure. Liquid suspensions of niraparib particles delivered by aerosol may be deposited in the airways by gravitational sedimentation, inertial impaction, and/or diffusion. Any suitable device for generating the aerosol may be used, including but not limited to metered dose inhalers (MDI), pressured metered dose inhalers (pMDI), nebulizers, and soft-mist inhalers.

In one embodiment, a dry powder composition of niraparib particles for therapeutic use may be aerosolized for pulmonary administration by inhalation, and the mass median aerodynamic diameter (MMAD) of the aerosolized dry powder composition may be any suitable diameter for use, and all embodiments disclosed herein may be used in the therapeutic methods of the disclosure. The dry powder composition delivered by aerosol may be deposited in the airways by gravitational sedimentation, inertial impaction, and/or diffusion. Any suitable device for generating the aerosol of the dry powder composition may be used in therapeutic methods of the disclosure, including but not limited to dry powder inhalers (DPI). An example of an excipient suitable for a dry powder inhalable composition includes but is not limited to lactose in grades suitable for inhalation. In one embodiment, the composition is a dry powder composition administered by inhalation via aerosolization.

In one embodiment, the composition comprises a dosage form of niraparib in suspension (i.e.: with a pharmaceutically acceptable carrier and any other components), in a dosage deemed suitable by an attending physician for an intended use. Any suitable dosage form may be used; in various non-limiting embodiments, the dosage form is adequate to provide about 0.01 mg/kg to about 50 mg/kg of body weight per day. In various further embodiments, the dosage form is adequate to provide about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg of body weight per day. The suspension can be administered as is or can be diluted with a diluent.

The compositions may be administered via any suitable route, including but not limited to orally, pulmonary, intraperitoneally, intra-tumorally, peri-tumorally, subcutaneous injection, intramuscular injection, administered into a mammary fat pad, or any other form of injection, as deemed most appropriate by attending medical personnel in light of all factors for a given subject.

In one embodiment, pulmonary administration comprises inhalation of a single dose of the niraparib particles, such as by nasal, oral inhalation, or both. The niraparib particles can be administered in two or more separate administrations (doses). In this embodiment, the particles may be formulated as an aerosol (i.e.: liquid droplets of a stable dispersion or suspension of the particles in a gaseous medium). Niraparib particles delivered by aerosol may be deposited in the airways by gravitational sedimentation, inertial impaction, and/or diffusion. Any suitable device for generating the aerosol may be used, including but not limited to metered dose inhalers (MDI), pressured metered dose inhalers (pMDI), nebulizers, and soft-mist inhalers.

In one specific embodiment, the methods comprise inhalation of niraparib particles aerosolized via nebulization. Nebulizers generally use compressed air or ultrasonic power to create inhalable aerosol droplets of the particles or suspensions thereof. In this embodiment, the nebulizing results in pulmonary delivery to the subject of aerosol droplets of the niraparib particles or suspension thereof.

In another embodiment, the methods comprise inhalation of niraparib particles aerosolized via a pMDI, wherein the particles or suspensions thereof are suspended in a suitable propellant system (including but not limited to hydrofluoroalkanes (HFAs) containing at least one liquefied gas in a pressurized container sealed with a metering valve. Actuation of the valve results in delivery of a metered dose of an aerosol spray of the niraparib particles or suspensions thereof.

In another embodiment, the methods comprise inhalation of a dry powder composition of niraparib via a DPI, wherein the dry powder composition contains niraparib particles alone without a carrier. In still another embodiment, the methods comprise inhalation of a dry powder composition of niraparib via a DPI, wherein the dry powder composition comprises niraparib particles and may include a pharmaceutically acceptable dry powder carrier comprising one or more dry powder excipients. An example of a dry powder excipient suitable for a dry powder inhalable composition includes but is not limited to lactose in grades suitable for inhalation.

A dosing period is that period of time during which a dose of niraparib particles in the composition or suspension is administered. The dosing period can be a single period of time during which the entire dose is administered, or it can be divided into two or more periods of time during each of which a portion of the dose is administered.

A post-dosing period is that period of time beginning after completion of a prior dosing period and ending after initiating a subsequent dosing period. The duration of the post-dosing period may vary according to a subject's clinical response to the niraparib. The suspension is not administered during the post-dosing period. A post-dosing period can last at least 7 days, at least 14 days, at least 21 days, at least 28 days, at least 35 days, at least 60 days or at least 90 days or longer. The post-dosing period can be kept constant for a subject or two or more different post-dosing periods can be used for a subject.

A dosing cycle includes a dosing period and a post-dosing period. Accordingly, the duration of a dosing cycle will be the sum of the dosing period and the post-dosing period. The dosing cycle can be kept constant for a subject or two or more different dosing cycles can be used for a subject.

In one embodiment, the administering is carried out more than once, and wherein each administration is separated in time by at least 21 days.

In another aspect, the disclosure provides methods for making niraparib particles, comprising:

(a) introducing (i) a solution comprising at least one solvent including but not limited to ethanol, methanol, hexafluoroisopropanol (HFIP), or combinations thereof, and at least one solute comprising niraparib or a pharmaceutically acceptable salt thereof into a nozzle inlet, and (ii) a compressed fluid into an inlet of a vessel defining a pressurizable chamber;

(b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 µm and 125 µm;

(c) contacting the atomized droplets with the compressed fluid, to cause depletion of the solvent from the atomized droplets, to produce niraparib particles comprising at least 95% niraparib or a pharmaceutically acceptable salt thereof, wherein the niraparib particles have a specific surface area (SSA) of at least 2.5 $m^2/g$ and optionally have mean particle size by volume distribution (Dv50) of from about 1.0 micron to about 10.0 microns in diameter, wherein steps (a), (b), and (c) are carried out under supercritical temperature and pressure for the compressed fluid.

The methods utilize a sonic energy source located directly in the output stream of the solute dissolved in the solvent. Any suitable source of sonic energy may be used that is compatible with the methods of the disclosure, including but not limited to sonic horn, a sonic probe, or a sonic plate. In various embodiments, the nozzle orifice is located between about 2 mm and about 20 mm, about 2 mm and about 18 mm, about 2 mm and about 16 mm, about 2 mm and about 14 mm, about 2 mm and about 12 mm, about 2 mm and about 10 mm, about 2 mm and about 8 mm, about 2 mm and about 6 mm, about 2 mm and about 4 mm, about 4 mm and about 20 mm, about 4 mm and about 18 mm, about 4 mm and about 16 mm, about 4 mm and about 14 mm, about 4 mm and about 12 mm, about 4 mm and about 10 mm, about 4 mm and about 8 mm, about 4 mm and about 6 mm, about 6 mm and about 20 mm, about 6 mm and about 18 mm, about 6 mm and about 16 mm, about 6 mm and about 14 mm, about 6 mm and about 12 mm, about 6 mm and about 10 mm, about 6 mm and about 8 mm, about 8 mm and about 20 mm, about 8 mm and about 18 mm, about 8 mm and about 16 mm, about 8 mm and about 14 mm, about 8 mm and about 12 mm, about 8 mm and about 10 mm, about 10 mm and about 20 mm, about 10 mm and about 18 mm, about 10 mm and about 16 mm, about 10 mm and about 14 mm, about 10 mm and about 12 mm, about 12 mm and about 20 mm, about 12 mm and about 18 mm, about 12 mm and about 16 mm, about 12 mm and about 14 mm, about 14 mm and about 20 mm, about 14 mm and about 18 mm, about 14 mm and about 16 mm, about 16 mm and about 20 mm, about 16 mm and about 18 mm, and about 18 mm and about 20 mm, from the sonic energy source. In further embodiments, the nozzle assembly of any embodiment of WO2016/197091 may be used.

Any suitable source of sonic energy may be used that is compatible with the methods of the disclosure, including but not limited to sonic horn, a sonic probe, or a sonic plate. In various further embodiments, the sonic energy source produces sonic energy with an amplitude between about 10% and about 100% of the total power that can be generated using the sonic energy source. In light of the teachings herein, one of skill in the art can determine an appropriate sonic energy source having a specific total power output to be used. In one embodiment, the sonic energy source has a total power output of between about 500 and about 900 watts; in various further embodiments, between about 600 and about 800 watts, about 650-750 watts, or about 700 watts.

In various further embodiments, the sonic energy source produces sonic energy with a power output between about 20% and about 100%, about 30% and about 100%, about 40% and about 100%, about 50% and about 100%, about 60% and about 100%, about 70% and about 100%, about 80% and about 100%, about 90% and about 100%, about 10% and about 90%, about 20% and about 90%, about 30% and about 90%, about 40% and about 90%, about 50% and about 90%, about 60% and about 90%, about 70% and about 90%, about 80% and about 90%, about 10% and about 80%, about 20% and about 80%, about 30% and about 80%, about 40% and about 80%, about 50% and about 80%, about 60% and about 80%, about 70% and about 80%, about 10% and about 70%, about 20% and about 70%, about 30% and about 70%, about 40% and about 70%, about 50% and about 70%, about 60% and about 70%, about 10% and about 60%, about 20% and about 60%, about 30% and about 60%, about 40% and about 60%, about 50% and about 60%, about 10% and about 50%, about 20% and about 50%, about 30% and about 50%, about 40% and about 50%, about 10% and about 40%, about 20% and about 40%, about 30% and about 40%, about 10% and about 30%, about 20% and about 30%, about 10% and about 20%, or about 10%, 20%, 30%, 40%, 50%, 60%, 70%, 80%, 90%, or about 100% of the total power that can be generated using the sonic energy source. In light of the teachings herein, one of skill in the art can determine an appropriate frequency to be utilized on the sonic energy source. In one embodiment, a frequency of between about 18 and about 22 kHz on the sonic energy source is utilized. In various other embodiments, a frequency of between about 19 and about 21 kHz, about 19.5 and about 20.5, or a frequency of about 20 kHz on the sonic energy source is utilized.

In various further embodiments, the nozzle orifice has a diameter of between about 20 µm and about 125 µm, about 20 µm and about 115 µm, about 20 µm and about 100 µm, about 20 µm and about 90 µm, about 20 µm and about 80 µm, about 20 µm and about 70 µm, about 20 µm and about 60 µm, about 20 µm and about 50 µm, about 20 µm and about 40 µm, about 20 µm and about 30 µm, between about 30 µm and about 125 µm, about 30 µm and about 115 µm, about 30 µm and about 100 µm, about 30 µm and about 90 µm, about 30 µm and about 80 µm, about 30 µm and about 70 µm, about 30 µm and about 60 µm, about 30 µm and about 50 µm, about 30 µm and about 40 µm, between about 40 µm and about 125 µm, about 40 µm and about 115 µm, about 40 µm and about 100 µm, about 40 µm and about 90 µm, about 40 µm and about 80 µm, about 40 µm and about 70 µm, about 40 µm and about 60 µm, about 40 µm and about 50 µm, between about 50 µm and about 125 µm, about 50 µm and about 115 µm, about 50 µm and about 100 µm, about 50 µm and about 90 µm, about 50 µm and about 80 µm, about 50 µm and about 70 µm, about 50 µm and about 60 µm, between about 60 µm and about 125 µm, about 60 µm and about 115 µm, about 60 µm and about 100 µm, about 60 µm and about 90 µm, about 60 µm and about 80 µm, about 60 µm and about 70 µm, between about 70 µm and about 125 µm, about 70 µm and about 115 µm, about 70 µm and about 100 µm, about 70 µm and about 90 µm, about 70 µm and about 80 µm, between about 80 µm and about 125 µm, about 80 µm and about 115 µm, about 80 µm and about 100 µm, about 80 µm and about 90 µm, between about 90 µm and about 125 µm, about 90 µm and about 115 µm, about 90 µm and about 100 µm, between about 100 µm and about 125 µm, about 100 µm and about 115 µm, between about 115 µm and about 125 µm, about 20 µm, 30 µm, 40 µm, 50 µm, 60 µm, 70 μm, 80 μm, 90 μm, 100 μm, 115 μm, or about 120 μm. The nozzle is inert to both the solvent and the compressed fluid used in the methods.

The solvent comprise ethanol, methanol, hexafluoroisopropanol (HFIP), or combinations thereof. The solvent should comprise at least about 80%, 85%, or 90% by weight of the overall solution.

The compressed fluid is capable of forming a supercritical fluid under the conditions used, and the solute that forms the particles is poorly soluble or insoluble in the compressed fluid. As is known to those of skill in the art, a supercritical fluid is any substance at a temperature and pressure above its critical point, where distinct liquid and gas phases do not exist. Steps (a), (b), and (c) of the methods of the disclosure are carried out under supercritical temperature and pressure for the compressed fluid, such that the compressed fluid is present as a supercritical fluid during these processing steps.

The compressed fluid can serve as a solvent for and can be used to remove unwanted components in the particles. Any suitable compressed fluid may be used in the methods of the disclosure; exemplary such compressed fluids are disclosed in U.S. Pat. Nos. 5,833,891 and 5,874,029. In one non-limiting embodiment, suitable supercritical fluid-forming compressed fluids and/or anti-solvents can comprise carbon dioxide, ethane, propane, butane, isobutane, nitrous oxide, xenon, sulfur hexafluoride and trifluoromethane. The anti-solvent recited in step (d) to cause further solvent depletion, is a compressed fluid as defined above, and may be the same compressed fluid used in steps (a-c), or may be different. In one embodiment, the anti-solvent used in step (d) is the same as the compressed fluid used in steps (a-c). In a preferred embodiment, the compressed fluid and the anti-solvent are both super-critical carbon dioxide.

In all cases, the compressed fluid and anti-solvent should be substantially miscible with the solvent while the niraparib should be substantially insoluble in the compressed fluid, i.e., niraparib, at the selected solvent/compressed fluid contacting conditions, should be no more than about 5% by weight soluble in the compressed fluid or anti-solvent, and preferably is essentially completely insoluble.

The supercritical conditions used in the methods of the disclosure are typically in the range of from 1× to about 1.4×, or 1× to about 1.2× of the critical temperature of the supercritical fluid, and from 1× to about 7×, or 1× to about 2×, of the of the supercritical pressure for the compressed fluid.

It is well within the level of those of skill in the art to determine the critical temperature and pressure for a given compressed fluid or anti-solvent. In one embodiment, the compressed fluid and anti-solvent are both super critical carbon dioxide, and the critical temperature is at least 31.1° C. and up to about 60° C., and the critical pressure is at least 1071 psi and up to about 1800 psi. In another embodiment, the compressed fluid and anti-solvent are both super critical carbon dioxide, and the critical temperature is at least 35° C. and up to about 55° C., and the critical pressure is at least 1070 psi and up to about 1500 psi. It will be understood by those of skill in the art that the specific critical temperature and pressure may be different at different steps during the processing.

Any suitable pressurizable chamber may be used, including but not limited to those disclosed in WO2016/197091 or in U.S. Pat. Nos. 5,833,891 and 5,874,029. Similarly, the steps of contacting the atomized droplets with the compressed fluid to cause depletion of the solvent from the droplets; and contacting the droplets with an anti-solvent to cause further depletion of the solvent from the droplets, to produce particles of the compound can be carried out under any suitable conditions, including but not limited to those disclosed in U.S. Pat. Nos. 5,833,891 and 5,874,029.

The flow rate can be adjusted as high as possible to optimize output but below the pressure limitations for the equipment, including the nozzle orifice. In one embodiment, the flow rate of the solution through the nozzle has a range from about 0.5 mL/min to about 30 mL/min. In various further embodiments, the flow rate is between about 0.5 mL/min to about 25 mL/min, 0.5 mL/min to about 20 mL/min, 0.5 mL/min to about 15 mL/min, 0.5 mL/min to about 10 mL/min, 0.5 mL/min to about 4 mL/min, about 1 mL/min to about 30 mL/min, about 1 mL/min to about 25 mL/min, about 1 mL/min to about 20 mL/min, 1 mL/min to about 15 mL/min, about 1 mL/min to about 10 mL/min, about 2 mL/min to about 30 mL/min, about 2 mL/min to about 25 mL/min, about 2 mL/min to about 20 mL/min, about 2 mL/min to about 15 mL/min, or about 2 mL/min to about 10 mL/min. The solution of drug subject to the flow rate can be any suitable concentration, such as between about 1 mg/ml and about 80 mg/ml.

In one embodiment, the methods further comprise receiving the plurality of particles through the outlet of the pressurizable chamber; and collecting the plurality of particles in a collection device, such as disclosed in WO2016/197091.

In another aspect, the disclosure provides niraparib particles prepared by the method of any embodiment or combination of embodiments of the disclosure.

EXAMPLES

| Description of Substances | |
|---|---|
| Compound Name: | Niraparib |
| Molecular Formula: | C19H20N4O |
| Molecular Weight: | 320.4 |

Material Testing

Particle Size Distribution (PSD) by Laser Diffraction
Imaging by Scanning Electron Microscopy (SEM)
Specific Surface Area (SSA) determination by BET Sorptometry
Crystalline/amorphous phase determination by Powder X-ray Diffraction (PXRD)
Bulk density analysis by modified USP <616> Bulk Density of Powders Method I
Dissolution using USP Apparatus 2

Study

1. Solvent solubility testing of niraparib in various solvents.
2. Demonstrate precipitating niraparib from three solvent systems, then analyzing the corresponding materials for/by PSD, SEM, PXRD, SSA, bulk density and dissolution.

The solubility of niraparib was tested in the following solvent mixtures:
  Ethanol alone,
  Methanol alone, and
  HFIP alone.

Four small scale precipitation runs were conducted with niraparib on an RC612B precipitation unit. The precipitates from the runs were analyzed by laser diffraction to determine PSD, SEM to support PSD data and determine shape/habit, BET sorptometry to determine the SSA, PXRD to determine crystalline/amorphous phase of the material, and bulk density analysis to identify additional physical characteristics of the precipitates. Dissolution testing was conducted comparing the dissolution rate of precipitated niraparib to the unprocessed drug substance.

Experimental Procedures

Material Receipt

Niraparib was obtained from BOC Sciences and stored in a temperature and humidity monitored cabinet.

Solvent Selection

Solubility in an organic solvent greater than ~8 mg/mL at room temperature was deemed adequate for further studies, with greater solvent solubility resulting in a decreased production time. Solubility was determined by visual observation and tested according to standard operating procedure.

Precipitation

Four small scale precipitates of niraparib were produced on the RC612B SCP unit according to standard operating procedure.

In one particular exemplary method, a solution of 20 mg/mL of niraparib was prepared in ethanol. The nozzle and a sonic probe were positioned in the pressurizable chamber approximately 9 mm apart. A stainless steel membrane filter with approximately 20 nm nominal rating was attached to the pressurizable chamber to collect the precipitated niraparib particles. The supercritical carbon dioxide was placed in the pressurizable chamber of the manufacturing equipment and brought to approximately 1200 psi at about 37.8° C. and a flow rate of 4 to 12 kg/hour. The sonic probe was adjusted to an amplitude of 60% of maximum output at a frequency of 20 kHz. The ethanol solution containing the niraparib was pumped through the nozzle at a flow rate of 2 mL/minute for approximately 12.5 minutes. The precipitated niraparib particles were then collected from the supercritical carbon dioxide as the mixture was pumped through the stainless steel mesh filter. The filter containing the particles of niraparib was opened and the resulting product was collected from the filter.

In one particular exemplary method, a solution of 67 mg/mL of niraparib was prepared in methanol. The nozzle and a sonic probe were positioned in the pressurizable chamber approximately 9 mm apart. A stainless steel membrane filter with approximately 20 nm nominal rating was attached to the pressurizable chamber to collect the precipitated niraparib particles. The supercritical carbon dioxide was placed in the pressurizable chamber of the manufacturing equipment and brought to approximately 1200 psi at about 37.5° C. and a flow rate of 4 to 12 kg/hour. The sonic probe was adjusted to an amplitude of 60% of maximum output at a frequency of 20 kHz. The methanol solution containing the niraparib was pumped through the nozzle at a flow rate of 2 mL/minute for approximately 4 minutes. The precipitated niraparib particles were then collected from the supercritical carbon dioxide as the mixture was pumped through the stainless steel mesh filter. The filter containing the particles of niraparib was opened and the resulting product was collected from the filter.

In one particular exemplary method, a solution of 100 mg/mL of niraparib was prepared in HFIP. The nozzle and a sonic probe were positioned in the pressurizable chamber approximately 9 mm apart. A stainless steel membrane filter with approximately 20 nm nominal rating was attached to the pressurizable chamber to collect the precipitated niraparib particles. The supercritical carbon dioxide was placed in the pressurizable chamber of the manufacturing equipment and brought to approximately 1200 psi at about 37.5° C. and a flow rate of 4 to 12 kg/hour. The sonic probe was adjusted to an amplitude of 60% of maximum output at a frequency of 20 kHz. The HFIP solution containing the niraparib was pumped through the nozzle at a flow rate of 2 mL/minute for approximately 2.5 minutes. The precipitated niraparib particles were then collected from the supercritical carbon dioxide as the mixture was pumped through the stainless steel mesh filter. The filter containing the particles of niraparib was opened and the resulting product was collected from the filter.

In one particular exemplary method, a solution of 50 mg/mL of niraparib was prepared in methanol. The nozzle and a sonic probe were positioned in the pressurizable chamber approximately 9 mm apart. A stainless steel membrane filter with approximately 20 nm nominal rating was attached to the pressurizable chamber to collect the precipitated niraparib particles. The supercritical carbon dioxide was placed in the pressurizable chamber of the manufacturing equipment and brought to approximately 1200 psi at about 38.0° C. and a flow rate of 4 to 12 kg/hour. The sonic probe was adjusted to an amplitude of 60% of maximum output at a frequency of 20 kHz. The methanol solution containing the niraparib was pumped through the nozzle at a flow rate of 2 mL/minute for approximately 100 minutes. The precipitated niraparib particles were then collected from the supercritical carbon dioxide as the mixture was pumped through the stainless steel mesh filter. The filter containing the particles of niraparib was opened and the resulting product was collected from the filter.

Analytical Testing

Following the precipitation runs of niraparib, the materials were analyzed for/by PSD, SEM, PXRD, SSA, bulk density and dissolution where applicable.

Solvent Selection

All results are shown in the Table 1.

Precipitation

The first precipitation run was conducted with ethanol (SC1), the second with methanol (SC2), respectively. The third run (SC3) was with HFIP. The precipitation run grid is shown in Table 1.

Particle Size Distribution

Particle size analyses were conducted on a Malvern Mastersizer™ 3000 using the Hydro MV™ dispersion unit. A non-validated general PSD method/dispersant method was used to analyze the niraparib samples. The sample preparation procedure performed was as follows: Weigh 10 to 20 mg of niraparib into a 30-mL vial, add 20 mL of ethyl acetate. Disperse the sample by vortexing then sonicating the suspension in an ultrasonic bath for 1 minute. Then transfer the sample suspension to the Malvern Hydro MV™ dispersion unit to obtain obscuration between 5 and 15%.

PSD results from a Dv10 of 0.601 μ to a Dv90 of 12.9μ were obtained. The Dv50 results for the 4 runs ranged from 2.32 μ to 5.74μ, significantly smaller than that seen with the raw material. Particle size distributions can be viewed in Table 1.

Scanning Electron Microscopy

Scanning electron microscopy was conducted on a Joel NeoScope™ SEM. Overall, imaging supports the particle size distribution results with varying distributions, as well as different particle shapes/habits. Exemplary SEM micrographs are presented in FIGS. 1-5.

Powder X-Ray Diffraction

Figure 6:
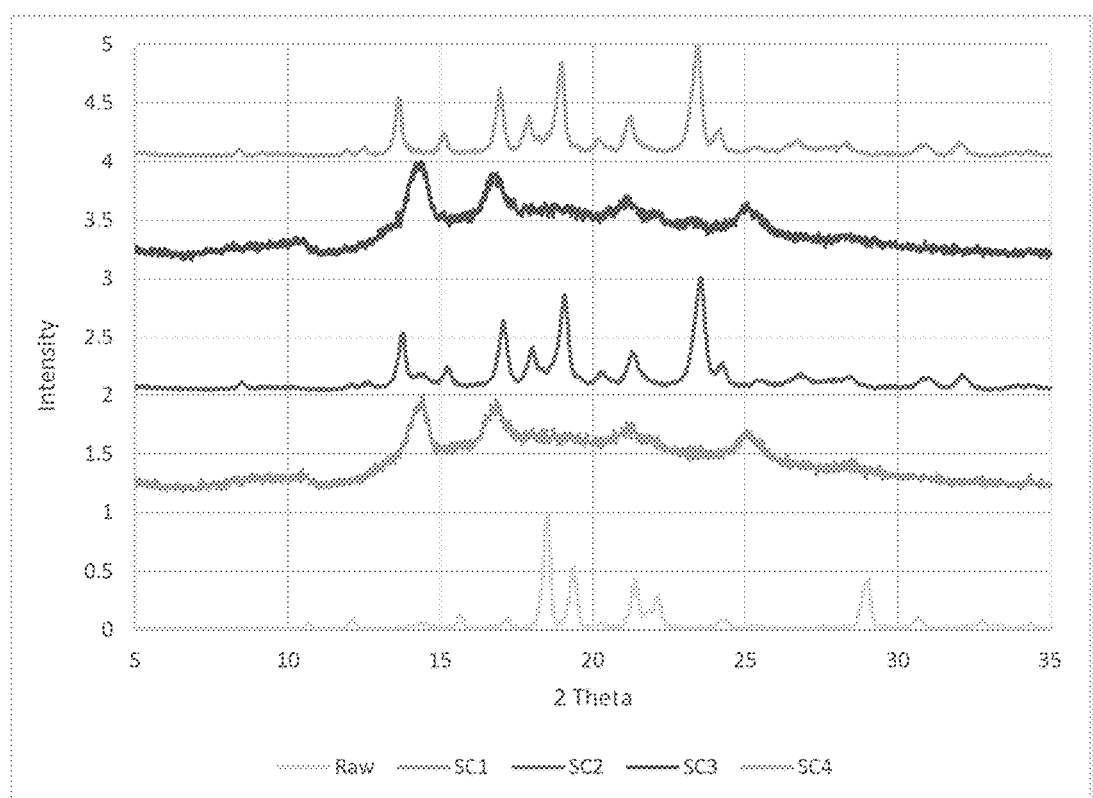
FIG. 6. Powder X-ray Diffraction Patterns for niraparib runs SC1-SC4 compared to the niraparib raw material FIG. 7. Graph showing dissolution of unprocessed niraparib (raw) or processed niraparib particles in 900 mL of 10% MeOH-Water at 50 rpm

Powder X-ray diffraction analyses were conducted on a Siemens D5000 X-ray Diffractometer. PXRD scanned from 5 to 35 2θ degrees at a rate of 0.02 2θ degrees/second and 1 second per step. The diffraction pattern overlay can be seen in FIG. 6.

Specific Surface Area

Surface area analyses were conducted on a Quantachrome NOVAtouch™ LX2 BET Sorptometer. Surface area results can be found in Table 1.

TABLE 1

| | | | | | |
|---|---|---|---|---|---|
| Project: SC2105 | | | | | |
| Drug: Niraparib | | | | | |
| Run # | Raw | SC1 | SC2 | SC3 | SC4 |
| Solvent(s) | | Ethanol | Methanol | HFIP | Methanol |
| Concentration (mg/ml) | | 20.1 | 66.7 | 100.1 | 50.0 |
| Solvent Volume (mL) | | 25 | 8 | 5 | 200 |
| Pressure (psi) | | 1190-1205 | 1190-1205 | 1190-1200 | 1200-1210 |
| Temperature (° C.) | | 37.7-37.9 | 37.5-37.5 | 37.5-37.7 | 37.5-38.4 |
| scCO2 Flowrate (gm/min) | | 70 | 70 | 70 | 70 |
| Solvent Flowrate (ml/min) | | 2 | 2 | 2 | 2 |
| Sonication (%) | | 60 | 60 | 60 | 60 |
| Nozzle Distance | | 9 mm | 9 mm | 9 mm | 9 mm |
| Yield | | | | | |
| Starting Mass (gm) | | 0.5024 | 0.5005 | 0.5005 | 10.0005 |
| Mass Collected (gm) | | 0.4685 | 0.3943 | 0.3521 | 5.74 |
| % Yield | | 93.25% | 78.78% | 70.35% | 57.40% |
| PSD - Masterisizer | | | | | |
| Dv-10 (μ) | 33.2 | 0.635 | 0.601 | 2.01 | 1.60 |
| Dv-50 (μ) | 103 | 2.66 | 2.32 | 5.74 | 4.66 |
| Dv-90 (μ) | 267 | 10.1 | 8.51 | 12.9 | 12.0 |
| Surface Area (m²/gm) | 0.70 | 18.56 | 22.15 | 5.12 | 11.96 |
| Bulk Density (gm/cm³) | 0.617 | — | — | — | 0.077 |
| Tapped Density (gm/cm³) | 0.741 | — | — | — | 0.119 |

Solubility Testing

The solubility was determined by using a shake-flask method. The drug was added in excess to each solution prepared in duplicate. The vials were placed on a mechanical shaker for 24 hours at 20-25° C. After shaking, solution was removed and filtered through a 0.45 μm PTFE syringe filter and analyzed by UV/Visible spectrophotometry. Results are shown in Table 2, which indicate that niraparib showed concentration dependent solubility.

TABLE 2

Solubility of Niraparib at Various Organic Solvent Concentrations

| | Concentration of Niraparib Found (μg/mL) | |
|---|---|---|
| Percent Organic | Methanol | Ethanol |
| 10% | 76.4 | 56.2 |
| 25% | 204 | 332 |

Dissolution Testing

Figure 7:
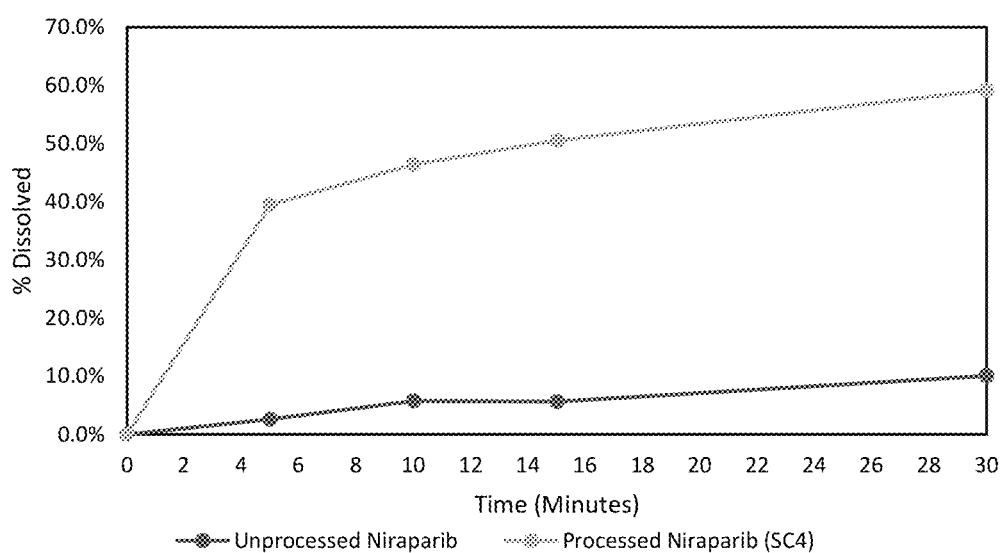

The selected media for dissolution testing was 900 mL of 10% methanol-water with a paddle speed of 50 rpm. To meet sink conditions, 20 mg of drug was directly added to the vessel. Two vessels contained processed SC4 material with specific surface area measurement of 11.96 $m^2/g$ and two vessels contained unprocessed material with specific surface area measurement of 0.70 $m^2/g$. Time points were taken at 5, 10, 15, and 30 minutes. At each time point, a 5-mL aliquot was drawn and immediately filtered with a 0.45 μm PTFE syringe filter, discarding the first 1 mL of filtrate. The solution was then analyzed by UV/Visible spectrophotometry at a wavelength of 240 nm. Dissolution profiles are represented in FIG. 7 and show good discrimination between the samples having different specific surface areas.

CONCLUSIONS

Niraparib was successfully precipitated from all solvent systems tested, with ethanol and methanol exhibiting the most promising results. The resulting niraparib particles exhibited significantly increased specific surface area and significantly improved dissolution properties.

We claim:

1. A composition, comprising particles comprising at least 95% by weight of niraparib, or a pharmaceutically acceptable salt thereof, wherein the particles have a specific surface area (SSA) of at least 5 $m^2/g$.

2. The composition of claim 1, wherein the particles have a SSA of at least 10 $m^2/g$.

3. The composition of claim 1, wherein the particles have a SSA of at least 15 $m^2/g$.

4. The composition of claim 1, wherein the particles have a SSA of between 5 $m^2/g$ and about 50 $m^2/g$.

5. The composition of claim 1, wherein the particles have a mean particle size by volume distribution (Dv50) of from about 1.0 micron to about 10.0 microns in diameter.

6. The composition of claim 1, wherein the particles have a mean bulk density (not tapped) between about 0.020 $g/cm^3$ and about 0.500 $g/cm^3$.

7. The composition of claim 1, wherein the particles have a mean tapped density of between about 0.050 $g/cm^3$ and about 0.600 $g/cm^3$.

8. The composition of claim 1, wherein the particles comprise at least 98%, by weight of niraparib, or a pharmaceutically acceptable salt thereof.

9. The composition of claim 1, wherein the particles are uncoated and exclude polymer, protein, polyethoxylated castor oil and polyethylene glycol glycerides composed of mono-, di- and triglycerides and mono- and diesters of polyethylene glycol.

10. The composition of claim 1, wherein the composition comprises a suspension further comprising a pharmaceutically acceptable liquid carrier.

11. The composition of claim 1, further comprising one or more components selected from the group consisting of polysorbate, methylcellulose, polyvinylpyrrolidone, mannitol, and hydroxypropyl methylcellulose.

12. The composition of claim 1, wherein the suspension is aerosolized, and the mass median aerodynamic diameter (MMAD) of aerosol droplets of the suspension between about 0.5 μm to about 6 μm diameter.

13. The composition of claim 1, wherein
   (a) the composition is a dry powder composition, wherein the dry powder composition does not comprise a carrier or any excipients, and wherein the dry powder composition is aerosolized, and the MMAD of the aerosolized dry powder composition between about 0.5 μm to about 6 μm in diameter, or
   (b) the composition is a dry powder composition, wherein the dry powder composition comprises a pharmaceutically acceptable dry powder carrier comprising one or more dry powder excipients, and wherein the dry powder composition is aerosolized, and the MMAD of the aerosolized dry powder composition is between about 0.5 μm to about 6 μm in diameter.

14. The composition of claim 1, wherein the pharmaceutically acceptable salt of niraparib comprises niraparib tosylate monohydrate.

15. A method for treating a tumor, comprising administering to a subject with a tumor an amount effective to treat the tumor of the composition of claim 1.

16. A method for making niraparib particles, comprising:
   (a) introducing (i) a solution comprising at least one solvent selected from the group consisting of ethanol, methanol, hexafluoroisopropanol (HFIP), or combinations thereof, and at least one solute comprising niraparib or a pharmaceutically acceptable salt thereof into a nozzle inlet, and (ii) a compressed fluid into an inlet of a vessel defining a pressurizable chamber;
   (b) passing the solution out of a nozzle orifice and into the pressurizable chamber to produce an output stream of atomized droplets, wherein the nozzle orifice is located between 2 mm and 20 mm from a sonic energy source located within the output stream, wherein the sonic energy source produces sonic energy with an amplitude between 10% and 100% during the passing, and wherein the nozzle orifice has a diameter of between 20 μm and 125 μm;
   (c) contacting the atomized droplets with the compressed fluid, to cause depletion of the solvent from the atomized droplets, to produce niraparib particles comprising at least 95% niraparib or a pharmaceutically acceptable salt thereof, wherein the niraparib particles have a specific surface area (SSA) of at least 5 $m^2/g$,
   wherein steps (a), (b), and (c) are carried out under supercritical temperature and pressure for the compressed fluid.

17. The method of claim 16, further comprising:
(d) contacting the compound particles produced in step (c) with an anti-solvent to cause further depletion of the solvent from the compound particles, wherein step (d) is carried out under supercritical temperature and pressure for the anti-solvent.

\* \* \* \* \*